US00PP34507P2

(12) United States Plant Patent
Ullrich

(10) Patent No.: US PP34,507 P2
(45) Date of Patent: Aug. 16, 2022

(54) ***ERYNGIUM* PLANT NAMED 'GEN E001'**

(50) Latin Name: *Eryngium L. alpinum*
Varietal Denomination: 'GEN E001'

(71) Applicant: TECNOVIV LLC, Miami, FL (US)

(72) Inventor: Clarisse Ullrich, Miami, FL (US)

(73) Assignee: Tecnoviv LLC, Miami, FL (US)

( * ) Notice: Subject to any disclaimer, the term of this patent is extended or adjusted under 35 U.S.C. 154(b) by 0 days.

(21) Appl. No.: 17/498,564

(22) Filed: Oct. 11, 2021

(51) Int. Cl.
*A01H 5/02* (2018.01)
*A01H 6/06* (2018.01)

(52) U.S. Cl.
USPC ..... Plt./361
CPC ..... *A01H 6/06* (2018.05)

(58) Field of Classification Search
USPC ..... Plt./361
CPC ..... A01H 5/02
See application file for complete search history.

(56) References Cited

U.S. PATENT DOCUMENTS

PP23,305 P2 1/2013 Star
PP27,092 P3 8/2016 Alcock

*Primary Examiner* — Kent L Bell
(74) *Attorney, Agent, or Firm* — Moses & Singer LLP; Milton Springut

(57) ABSTRACT

A new and distinct variety of *Eryngium* plant, botanically known as *Eryngium L. alpinum*, and hereinafter referred to by the name 'GEN E001', characterized by its upright and relatively compact plant habit; upright growth habit; branched in upper part; strong flowering stems; a single-type inflorescence, and good cut flower performance.

4 Drawing Sheets

Latin name of the genus and species: *Eryngium L. alpinum.*

Variety denomination: 'GEN E001'.

BACKGROUND OF THE INVENTION

The present invention relates to a new and distinct variety of *Eryngium* plant botanically known as *Eryngium L. alpinum. Eryngium* is a genus of flowering plants in the family Apiaceae. *Eryngium* is distributed in temperate climates throughout the world. It has a wide diversity of morphology and is known for its floral bracts.

*Eryngium* are characterized as herbaceous perennial plants, hemicryptophytes, a bit rough with stiff branches, thorny leaves and rosette-forming. They are commonly called alpine sea holly, alpine eryngo or queen of the Alps. This species has become extremely rare, even at risk of extinction in some localities due to its beauty and consequent indiscriminate collection. It is native to the Alps, Jura, and northwest of the Balkan Mountains. The species is used as a rockery plant and also for the formation of bouquets. In 1993 dried *Eryngium* were selling at $2.75 per bunch wholesale, while the retail price was $2 to $4 a bunch of 10 stems. A field bunch was $3.30 wholesale price. Currently 5 stems can sell for around $4.50.

SUMMARY OF THE INVENTION

The present disclosure relates to a new and distinct variety of *Eryngium* plant, botanically known as *Eryngium L. alpinum*, and hereinafter referred to by the name 'GEN E001'. Plants of the new *Eryngium* have not been observed under all possible environmental conditions. The phenotype may vary somewhat with variations in environment such as temperature and light intensity, without, however, any variance in genotype.

'GEN E001' was produced at El Quinche, Pichincha, Ecuador, and its botanical description was obtained at the same place. 'GEN E001' was propagated by roots in vivo. The origin of the variety was by conventional breeding (hand pollination) between two lines of the breeding germplasm bank. The plant was selected because it has specific parameters of commercial interest. The first selection was in 2009 year and it was first asexually reproduced in 2010 by roots at El Quinche, Pichincha, Ecuador. The parents were collected in different parts of the world, they are part of a germplasm bank that we maintain to use in different crosses.

The following traits of the new cultivar have been repeatedly observed and are determined to be the unique characteristics of 'GEN E001'. These characteristics in combination distinguish 'GEN E001' as a new and distinct variety of *Eryngium:*

1. Upright growth habit, perennial herb
2. Ascending to sub-erect branching habit
3. Basal leaves with topped cone-shaped flower heads
4. Stem solid, branched in upper part
5. The inflorescence size is larger than usual
6. Smaller flowers than the female parent.
7. Shorter and thicker stems and larger flowers as compared with the male parent.
8. The plant is more vigorous and has less odor than other *Eryngium* plants. The greater vigor is in the strong stems and inflorescence, the foliage is resistant and strong, and the inflorescence does not lose color.

BRIEF DESCRIPTION OF THE DRAWINGS

The accompanying photographs depict characteristics and illustrate the overall appearance of the new *Eryngium* plant.

The plant was photographed at about one year old. The photographs show the colors as true as it is reasonably possible to obtain in colored reproductions of this type. Colors in the photographs may differ slightly from the color values cited in the detailed botanical description which accurately describe the colors of the new *Eryngium* plant.

DETAILED BOTANICAL DESCRIPTION

Figure 1:
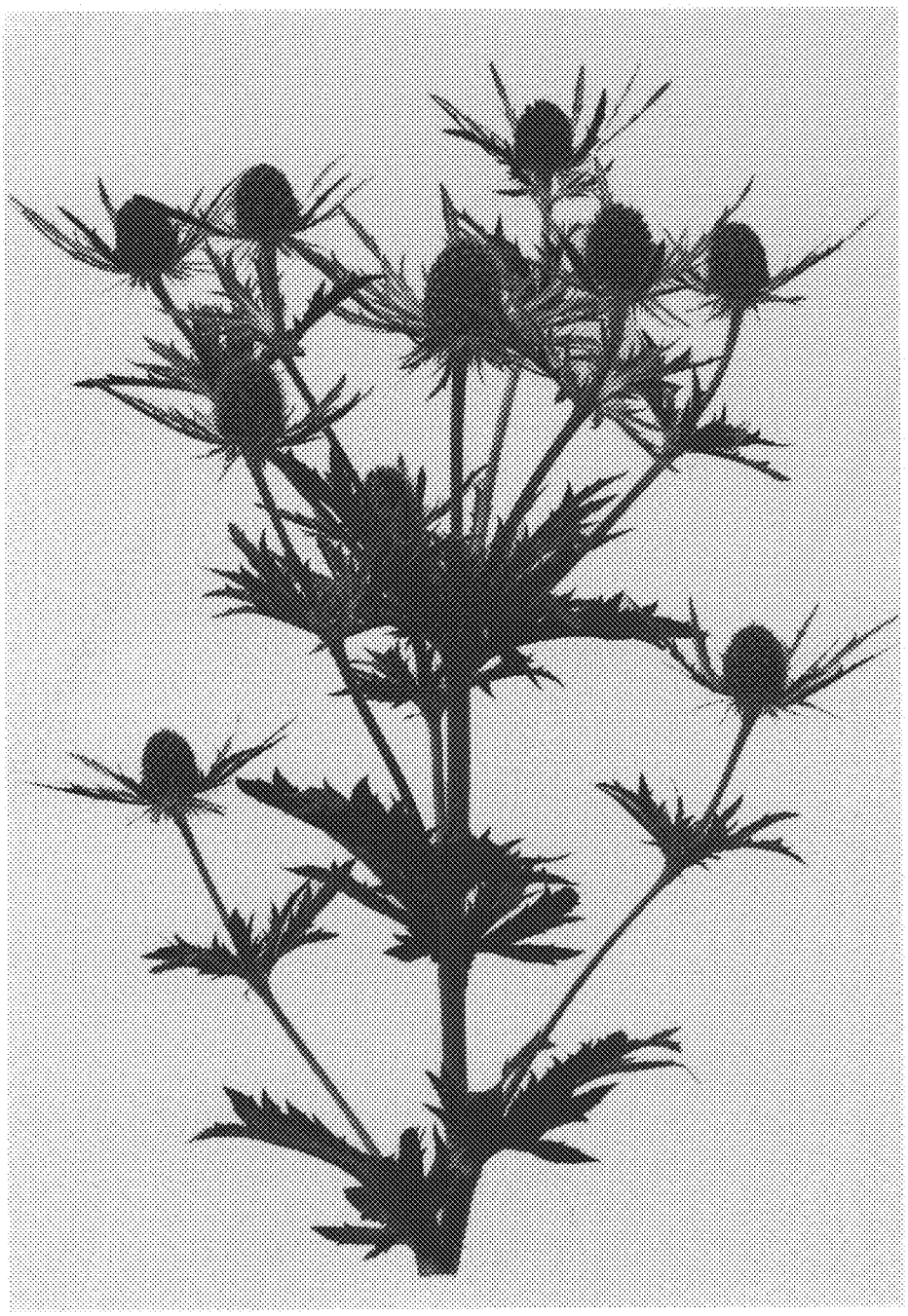
FIG. 1 is a photograph of a side view of typical flowering stem of 'GEN E001' like a field plant, in a Frigid zone to tropical, cultivated in El Quinche, Ecuador, 2500 mamsl (meters above mean sea level).
Figure 2:
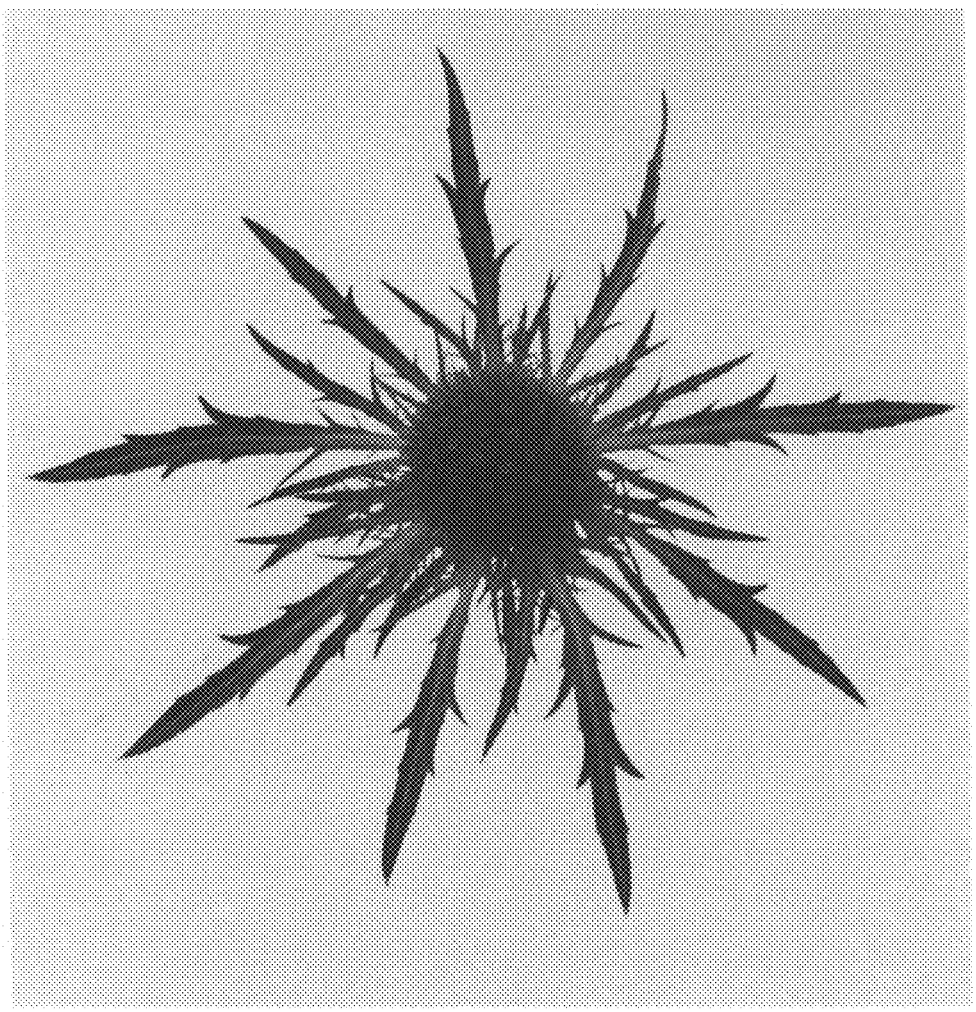
FIG. 2 is a photograph showing a close-up view of a typical developed flower of 'GEN E001'.
Figure 3:
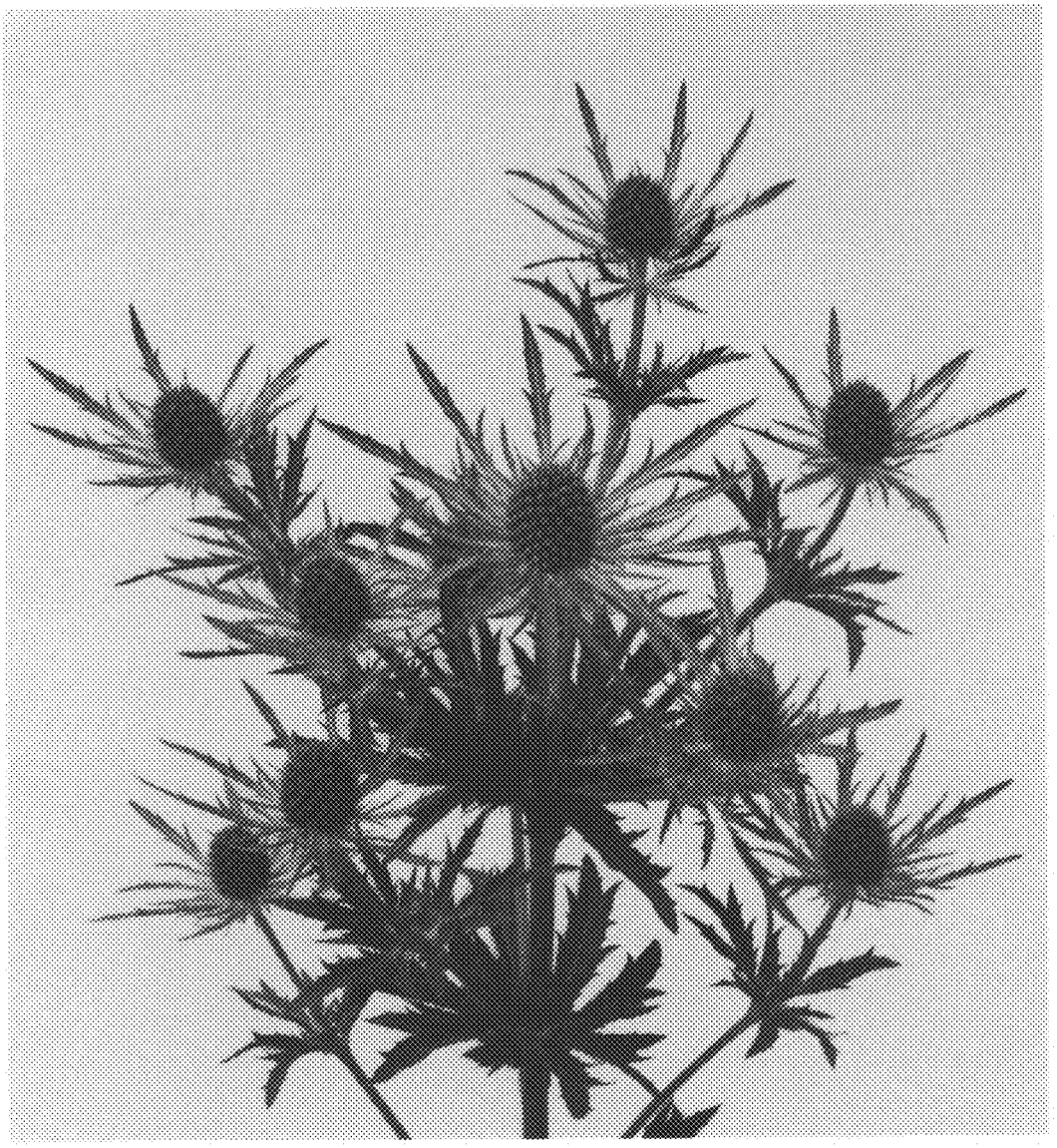
FIG. 3 is a photograph of a close-up view of a typical inflorescence of 'GEN E001'.
Figure 4:
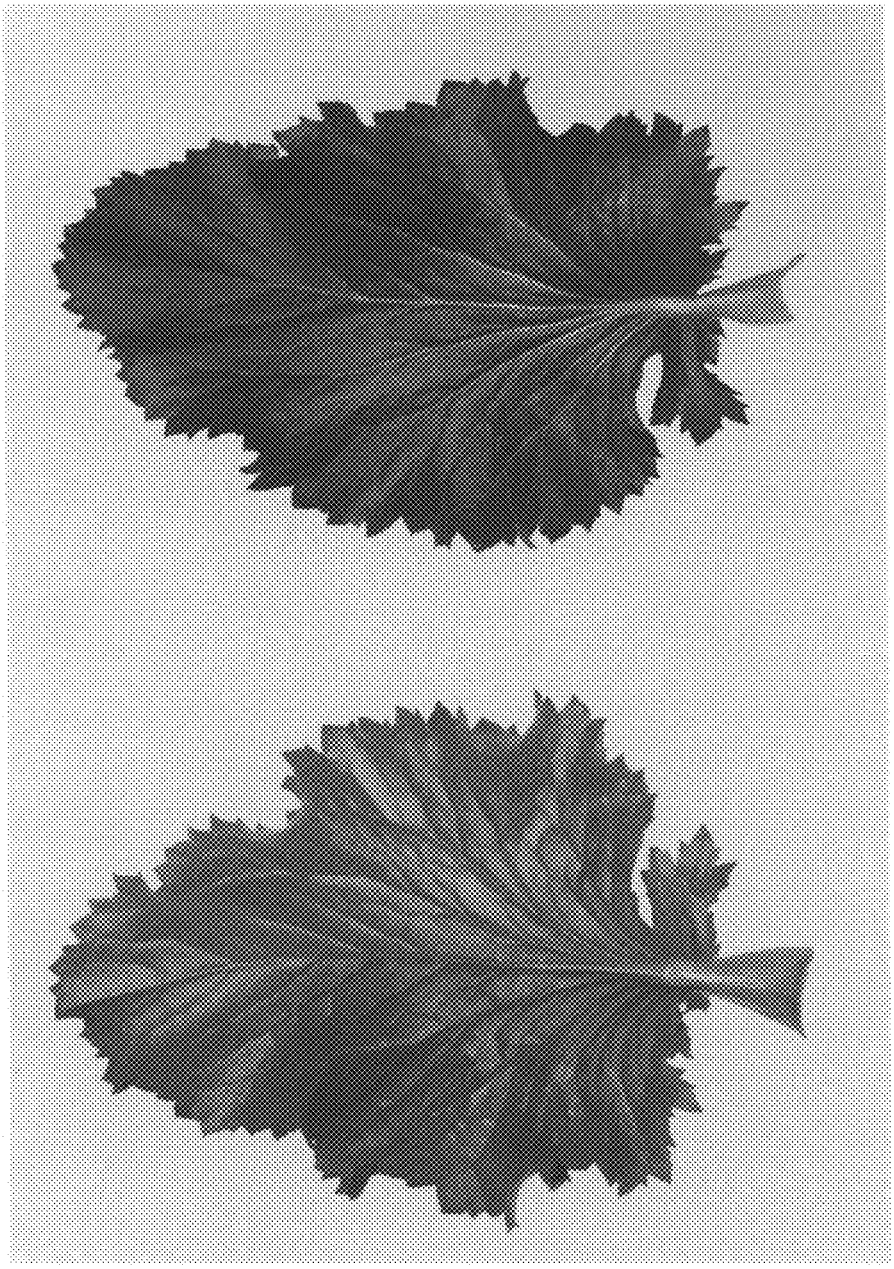
FIG. 4 is a photograph of a close-up view of a typical leaf of 'GEN E001'.

The following is a detailed botanical description of a new and distinct variety of *Eryngium* plant, botanically known as *Eryngium L. alpinum*, based upon observations of plants of about one year old in El Quinche, Ecuador, 2500 mamsl (meters above mean sea level), with 3 irrigation passes of 1 minute, temperatures in the range of about 8° C. to about 33° C. in May 2021.

Those skilled in the art will appreciate that certain characteristics will vary with older or, conversely, with younger plants. 'GEN E001' has not been observed under all possible environmental conditions. Where dimensions, sizes, colors, and other characteristics are given, it is to be understood that such measurements are approximations or averages set forth as accurately as practicable. The phenotype of the cultivar may differ from the descriptions set forth herein with variations in environmental, climatic, and cultural conditions. Color notations are based on The Royal Horticultural Society Colour Chart, The Royal Horticultural Society, London, Sixth Edition 2015.

Botanical classification: *Eryngium L. alpinum* 'GEN E001'.

Parentage:

- *Female, or seed, parent.*—Line Y2 (mother) is characterized by small flowers, many flowers, easy induction, and excellent propagation. Has not been patented.
- *Male, or pollen, parent.*—Line Y3 (father) is characterized as having big flower, many flowers, blue flower, soft leaves, not bad smell. It has not been patented.

Propagation: Propagation by Roots (in vivo) New plants are obtained by cutting the roots. It took about 14 weeks to produce a plant. The plant was grown at temperatures between about 15° C. to about 25° C. and it took about 8 weeks to initiate new roots.

Root description:

- *Rooting habit.*—Deep.
- *Time to initiate roots, summer.*—About 8 weeks with temperatures in the range of about 8° C. to about 47° C. and humidity between about 8.3% HR to about 82.6% HR.
- *Time to produce a rooted young plant, summer.*—About 14 weeks with temperatures in the range of about 8° C. to about 47° C. and humidity between about 8.3% HR to about 82.6% HR.
- *Root description.*—Robust.
- *Rooting habit.*—Deep.

Plant description:

- *Plant form/growth habit.*—Upright, perennial herb, larger and more vigorous than other varieties known to the Inventor.
- *Productivity.*—180 stems/m2/year.
- *Branching habit.*—Ascending to sub-erect.
- *Plant height.*—About 105 cm.
- *Plant width (diameter or spread).*—About 42 cm.
- *USDA hardiness zone.*—Winter hardy at USDA zone 2 and higher.

Stem description:

- *Length.*—About 32 cm.
- *Diameter.*—About 0.6 cm.
- *Internode length.*—About 9 cm.
- *Aspect.*—Fibrous.
- *Strength.*—Strong.
- *Texture.*—Woody.
- *Color.*—Grey-Brown Group NN 199A to Yellow Green Group 146 B.

Lateral branches:

- *Quantity.*—8-15.
- *Length.*—About 32 cm.
- *Diameter.*—About 0.6 cm.
- *Internode length.*—About 9 cm.
- *Texture.*—Woody, Fibrous.
- *Strength.*—Strong.
- *Color.*—Grey-Brown Group NN 199A to Yellow Green Group 146 B.
- *Shape.*—Cylindrical.

Leaf description:

- *Arrangement.*—Alternate, single.
- *Leaf length.*—About 20 cm.
- *Leaf width.*—About 15 cm.
- *Leaf shape.*—Elliptic, ovate.
- *Leaf apex.*—Obtuse, upper leaves lobed.
- *Leaf base.*—Heart shaped.
- *Leaf margin.*—Serrate.
- *Leaf texture, upper and lower surfaces.*—Rough.
- *Leaf venation pattern.*—Palmate.

Leaf color:

- *Developing Leaves, upper surface, venation color.*—Yellow Green Group 144A; Venation color: Yellow Green Group 144C.
- *Developing Leaves, lower surface, venation color.*—Yellow Green Group 144B; Venation color: Yellow Green Group 144C.
- *Fully expanded leaves, upper surface, venation color.*—Green Group NN 137A; Venation color: Yellow Green Group 144C.
- *Fully expanded leaves, lower surface; venation color.*—Green Group 137D; Venation color: Yellow Green Group 144C.

Petioles, leaves:

- *Length.*—About 19.3 cm.
- *Diameter.*—About 0.45 cm.
- *Texture, upper surface.*—Woody, Fibrous.
- *Texture, lower surface.*—Woody, Fibrous.
- *Color, upper surface.*—Yellow Green Group 144B.
- *Color, lower surface.*—Yellow Green Group 144B.

Flower description:

- *Flower type and arrangement.*—Type is single; arrangement: Inflorescence-Umbel.
- *Flowering season.*—Any time of the year in Ecuador.
- *Flower diameter.*—About 0.45 cm.
- *Flower depth (height).*—About 0.93 cm.

*Flower longevity.*—15-18 days.
*Fragrance.*—Strong.
*Inflorescence height, terminal inflorescences.*—Flower heads of the primary branches: about 3 cm. Flower heads of the secondary branches: about 2.5 cm. Umbel Inflorescence: about 30 cm.
*Inflorescence diameter, terminal inflorescences.*—
*Flower heads of the primary branches.*—About 2.3 cm.
*Flower heads of the secondary branches.*—About 2.3 cm.
*Umbel inflorescence.*—About 34 cm.

Flower buds:
*Shape.*—Cup Shaped.
*Length.*—About 4.21 cm.
*Diameter.*—About 1.41 cm.
*Color.*—Green Group 143B to Green Group 143D.
*Rate of opening.*—15 days.

Petals:
*Arrangement.*—Pentamerous, valvate.
*Quantity.*—5.
*Length.*—About 1.5 mm.
*Width.*—About 0.6 mm.
*Shape.*—Oblong.
*Apex.*—Emarginate.
*Base.*—Truncate.
*Margin.*—Entire.
*Texture, upper surfaces.*—Soft, smooth.
*Texture, lower surfaces.*—Soft smooth.
*Color.*—When opening, upper surface: Green Group 143 B to Green Group 143 D. When opening, lower surface: Green Group 143 B to Green Group 143 D. Fully opened, upper surface: Base: Green-White Group 157B. Tip: Violet-Blue Group N89C. Fully opened, lower surface: Base: Green-White Group 157B. Tip: Violet-Blue Group N89C.

Sepals:
*Quantity per flower.*—5.
*Length.*—About 4 mm.
*Width.*—About 1.1 mm.
*Shape.*—Triangulate.
*Apex.*—Aristate.
*Base.*—Cuneate.
*Margin.*—Entire.
*Texture, upper and lower surfaces.*—Smooth.
*Color.*—When opening, upper surface: Green Group 143B to Green Group 143D. When opening, lower surface: Green Group 143B to Green Group 143D. When opened, upper surface: Yellow Green Group 147A to Violet Blue Group 90D. Base: Yellow Green Group 145 C. When opened, lower surface: Yellow Green Group 147A to Violet Blue Group 90D. Base: Yellow Green Group 145 C.

Inflorescence bracts:
*Arrangement.*—Making an unusual teasel-like collar around the central flower.
*Range of bracts per inflorescence.*—23 to 30.
*Length.*—Flower heads of the primary branches: about 6 cm. Flower heads of the secondary branches: about 5 cm. Umbel Inflorescence: about 9 cm.
*Width.*—Flower heads of the primary branches: about 2.5 cm. Flower heads of the secondary branches: about 5 cm. Umbel Inflorescence: about 9 cm.
*Shape.*—Lanceolate involucral bracts fuse forming a cup-shaped structure.
*Apex.*—Pointed-Sharp.
*Base.*—Truncate.
*Margin.*—Dentate, large, spiny teeth.
*Texture, upper and lower surfaces.*—Rough.
*Color, upper surface.*—Flower heads: Violet Group 85C to Green Group NN 137B. Umbel Inflorescence: Yellow Green Group 147A.
*Color, lower surface.*—Flower heads: Yellow Green Group 147A. Umbel Inflorescence: Green Group 137B.

Peduncles:
*Length, terminal peduncles.*—Main peduncle: about 9 cm. Lateral peduncles: about 10 cm.
*Diameter, terminal peduncles.*—
*Main peduncle.*—About 0.8 cm.
*Lateral peduncles.*—About 0.5 cm.
*Angle main peduncle.*—0°, Its erect.
*Angle lateral peduncles.*—29°-45°.
*Strength.*—Strong.
*Texture.*—Woody, Fibrous.
*Color.*—Green Group 138B to Yellow Green Group 145D.

Reproductive organs:
Stamens:
*Quantity/arrangement.*—5.
*Filament color.*—Yellow Green Group 145C.
*Anther shape.*—Bilocular, Sagittate.
*Anther length.*—About 1.1 mm.
*Anther color.*—Yellow Green Group 145C.
*Pollen amount.*—Moderate.
*Pollen color.*—White Group 155C.

Pistils:
*Quantity.*—2.
*Pistil length.*—About 4.0 mm.
*Style length.*—About 4.0 mm.
*Style color.*—Yellow-Green Group 145 C.
*Stigma shape.*—Undifferentiated.
*Stigma color.*—Violet-Blue Group 90A.
*Ovary color.*—Yellow Green Group 150B.
*Receptacle height.*—About 2.5 mm.
*Receptacle diameter.*—About 1.45 mm.
*Receptacle shape.*—Cup Shaped.
*Receptacle texture.*—Smooth.
*Receptacle color.*—Green Group 143 B.
*Fruits and seeds.*—Fruits and seeds have not been observed on plants of the new *Eryngium.*

What is claimed is:

1. A new and distinct variety of *Eryngium* plant named 'GEN E001' as herein illustrated and described.

* * * * *